(12) United States Patent
Reed et al.

(10) Patent No.: US 6,231,869 B1
(45) Date of Patent: *May 15, 2001

(54) COMPOUNDS AND METHODS FOR THE DIAGNOSIS AND TREATMENT OF EHRLICHIA INFECTION

(75) Inventors: Steven G. Reed, Bellevue; Michael J. Lodes, Seattle; Raymond Houghton, Bothell, all of WA (US)

(73) Assignee: Corixa Corporation, Seattle WA ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/821,324

(22) Filed: Mar. 21, 1997

(51) Int. Cl.⁷ .............................. A61K 39/02; C12Q 1/68; C07H 21/04
(52) U.S. Cl. ...................... 424/234.1; 435/6; 536/23.7; 536/24.32; 536/24.33
(58) Field of Search .............................. 424/234.1; 435/6; 536/23.7, 24.32, 24.33

(56) References Cited

FOREIGN PATENT DOCUMENTS

| WO 96/39484 | 12/1996 | (WO) | .............................. C12N/1/20 |
| WO 98/14584 | 4/1998 | (WO) | .............................. C12N/15/31 |
| WO 98/42740 | 10/1998 | (WO) | . |
| WO 98/49313 | 11/1998 | (WO) | . |

OTHER PUBLICATIONS

Asanovich et al., "Partial Characterization of Cloned Genes Encoding Immunoreactive Proteins of *Ehrlichia equi* and the Agent of Human Granulocytic Ehrlichiosis," Abstracts of the General Meeting of the American Society for Microbiology: Abstract No. D–22, 1996.

Dumler et al., "Serologic Cross–Reactions among *Ehrlichia equi, Ehrlichia phagocytophila*, and Human granulocytic Ehrlichia," *Journal of Clinical Microbiology* 33(5): 1098–1103, 1995.

Palmer et al., "The Immunoprotective *Anaplasma marginale* Major Surface Protein 2 Is Encoded by a Polymorphic Multigene Family," *Infection And Immunity* 62(9): 3808–3816, 1994.

Magnarelli et al., "Coexistence of Antibodies to Tick–Borne Pathogens of Babesiosis, Ehrlichiosis, and Lyme Borreliosis in Human Sera," *Journal Of Clinical Microbiology* 33(11): 3054–3057, 1995.

*Primary Examiner*—Rodney P. Swart
(74) *Attorney, Agent, or Firm*—Seed Intellectual Property Law Group PLLC

(57) ABSTRACT

Compounds and methods for the diagnosis and treatment of Ehrlichia infection, in particular human granulocytic ehrlichiosis, are disclosed. The compounds provided include polypeptides that contain at least one antigenic portion of an Ehrlichia antigen and DNA sequences encoding such polypeptides. Pharmaceutical compositions and vaccines comprising such polypeptides or DNA sequences are also provided. Diagnostic kits containing such polypeptides or DNA sequences and a suitable detection reagent may be used for the detection of Ehrlichia infection in patients and biological samples. Antibodies directed against such polypeptides are also provided.

3 Claims, 5 Drawing Sheets

COMPOUNDS AND METHODS FOR THE DIAGNOSIS AND TREATMENT OF EHRLICHIA INFECTION

TECHNICAL FIELD

The present invention relates generally to the detection and treatment of Ehrlichia infection. In particular, the invention is related to polypeptides comprising an Ehrlichia antigen and the use of such polypeptides for the serodiagnosis and treatment of Human granulocytic ehrlichiosis (HGE).

BACKGROUND OF THE INVENTION

Human granulocytic ehrlichiosis (HGE) is an illness caused by a rodent bacterium which is generally transmitted to humans by the same tick that is responsible for the transmission of Lyme disease and babesiosis, thereby leading to the possibility of co-infection with Lyme disease, babesiosis and HGE from a single tick bite. The bacterium that causes HGE is believed to be quite widespread in parts of the northeastern United States and has been detected in parts of Europe. While the number of reported cases of HGE infection is increasing rapidly, infection with Ehrlichia, including co-infection with Lyme disease, often remains undetected for extended periods of time. HGE is a potentially fatal disease, with the risk of death increasing if appropriate treatment is delayed beyond the first few days after symptoms occur. In contrast, deaths from Lyme disease and babesiosis are relatively rare.

The preferred treatments for HGE, Lyme disease and babesiosis are different, with penicillins, such as doxycycline and amoxicillin, being most effective in treating Lyme disease, anti-malarial drugs being preferred for the treatment of babesiosis and tetracycline being preferred for the treatment of ehrlichiosis. Accurate and early diagnosis of Ehrlichia infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. The only tests currently available for the diagnosis of HGE infection are indirect fluorescent antibody staining methods for total immunoglobulins to Ehrlichia causative agents and polymerase chain reaction (PCR) amplification tests. Such methods are time-consuming, labor-intensive and expensive. There thus remains a need in the art for improved methods for the detection of Ehrlichia infection, particularly as related to HGE. The present invention fulfills this need and further provides other related advantages.

SUMMARY OF THE INVENTION

The present invention provides compositions and methods for the diagnosis and treatment of Ehrlichia infection and, in particular, for the diagnosis and treatment of HGE. In one aspect, polypeptides are provided comprising an immunogenic portion of an Ehrlichia antigen, particularly one associated with HGE, or a variant of such an antigen that differs only in conservative substitutions and/or modifications. In one embodiment, the antigen comprises an amino acid sequence encoded by a DNA sequence selected from the group consisting of (a) sequences recited in SEQ ID NO: 1–7, 15–22, 31, 34 and 36; (b) the complements of said sequences; and (c) sequences that hybridize to a sequence of (a) or (b) under moderately stringent conditions.

In another aspect, the present invention provides an antigenic epitope of an Ehrlichia antigen comprising an amino acid sequence of SEQ ID NO: 30, together with polypeptides comprising at least two such antigenic epitopes, the epitopes being contiguous.

In a related aspect, DNA sequences encoding the above polypeptides, recombinant expression vectors comprising one or more of these DNA sequences and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope.

In further aspects of the subject invention, methods and diagnostic kits are provided for detecting Ehrlichia infection in a patient. In one embodiment, the method comprises: (a) contacting a biological sample with at least one of the above polypeptides, antigenic epitopes or fusion proteins; and (b) detecting in the sample the presence of antibodies that bind to the polypeptide, antigenic epitope or fusion protein, thereby detecting Ehrlichia infection in the biological sample. Suitable biological samples include whole blood, sputum, serum, plasma, saliva, cerebrospinal fluid and urine. The diagnostic kits comprise one or more of the above polypeptides, antigenic epitopes or fusion proteins in combination with a detection reagent.

The present invention also provides methods for detecting Ehrlichia infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the oligonucleotide primers. In one embodiment, the oligonucleotide primer comprises at least about 10 contiguous nucleotides of a DNA sequence encoding the above polypeptides.

In a further aspect, the present invention provides a method for detecting Ehrlichia infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of Ehrlichia infection.

Within other aspects, the present invention provides pharmaceutical compositions that comprise one or more of the above polypeptides or antigenic epitopes, or a DNA molecule encoding such polypeptides, and a physiologically acceptable carrier. The invention also provides vaccines comprising one or more of the inventive polypeptides or antigenic epitopes and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
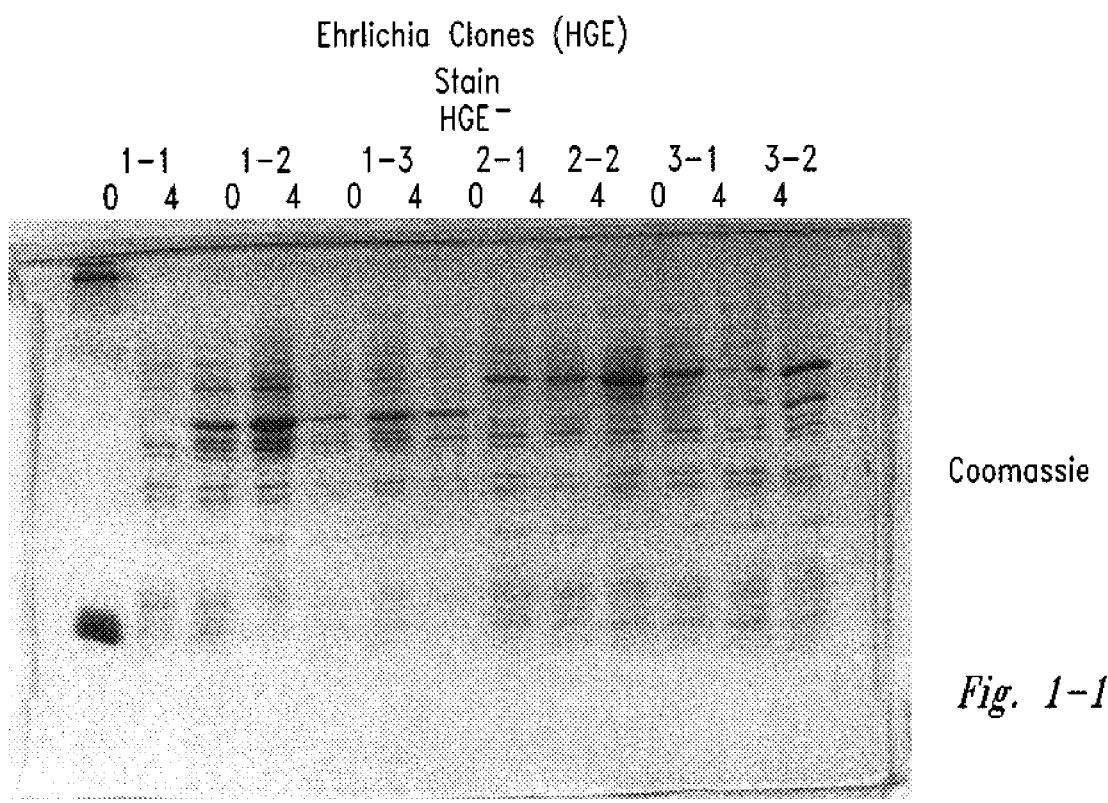
FIG. 1 shows the results of Western blot analysis of representative Ehrlichia antigens of the present invention.
Figures 1, 2:
Figures 1, 2, 3:
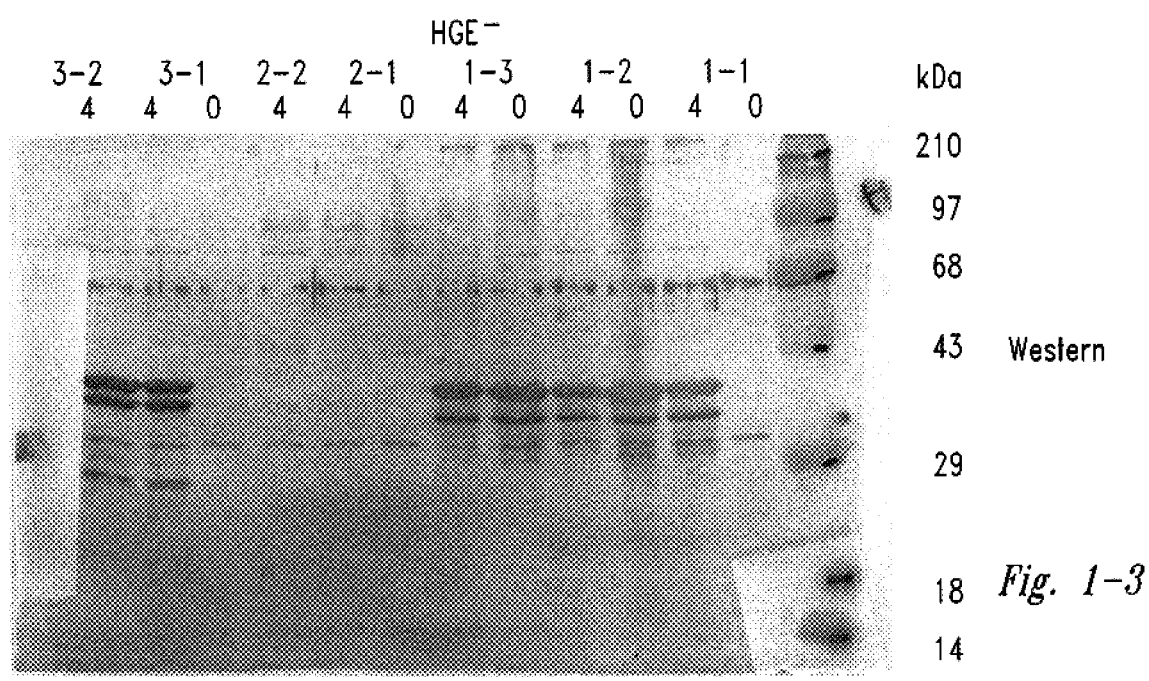

As noted above, the present invention is generally directed to compositions and methods for the diagnosis and treatment of Ehrlichia infection, in particular HGE. In one aspect, the compositions of the subject invention include polypeptides that comprise at least one immunogenic portion of an Ehrlichia antigen, or a variant of such an antigen that differs only in conservative substitutions and/or modifications.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native Ehrlichia antigen or may be heterologous, and such sequences may (but need not) be immunogenic.

An "immunogenic portion" of an antigen is a portion that is capable of reacting with sera obtained from an Ehrlichia-infected individual (i.e., generates an absorbance reading with sera from infected individuals that is at least three standard deviations above the absorbance obtained with sera from uninfected individuals, in a representative ELISA assay described herein). Polypeptides comprising at least an immunogenic portion of one or more Ehrlichia antigens as described herein may generally be used, alone or in combination, to detect HGE in a patient.

The compositions and methods of this invention also encompass variants of the above polypeptides. A "variant," as used herein, is a polypeptide that differs from the native antigen only in conservative substitutions and/or modifications, such that the antigenic properties of the polypeptide are retained. Such variants may generally be identified by modifying one of the above polypeptide sequences, and evaluating the antigenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In specific embodiments, the subject invention discloses polypeptides comprising at least an immunogenic portion of an Ehrlichia antigen (or a variant of such an antigen), that comprises one or more of the amino acid sequences encoded by (a) a DNA sequence selected from the group consisting of SEQ ID NO: 1–7, 15–22, 31, 34 and 36, (b) the complements of such DNA sequences or (c) DNA sequences substantially homologous to a sequence in (a) or (b).

The Ehrlichia antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5×and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

In general, Ehrlichia antigens, and DNA sequences encoding such antigens, may be prepared using any of a variety of procedures. For example, DNA molecules encoding Ehrlichia antigens may be isolated from an Ehrlichia genomic or cDNA expression library by screening with sera from HGE-infected individuals as described below in Example 1, and sequenced using techniques well known to those of skill in the art. DNA molecules encoding Ehrlichia antigens may also be isolated by screening an appropriate Ehrlichia expression library with anti-sera (e.g., rabbit) raised specifically against Ehrlichia antigens.

Antigens may be induced from such clones and evaluated for a desired property, such as the ability to react with sera obtained from an HGE-infected individual as described herein. Alternatively, antigens may be produced recombinantly, as described below, by inserting a DNA sequence that encodes the antigen into an expression vector and expressing the antigen in an appropriate host. Antigens may be partially sequenced using, for example, traditional Edman chemistry. See Edman and Berg, *Eur. J Biochem.* 80:116–132, 1967.

DNA sequences encoding antigens may also be obtained by screening an appropriate Ehrlichia cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

Immunogenic portions of Ehrlichia antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of an Ehrlichia antigen generates at least about 20%, and preferably about 100%, of the signal induced by the full length antigen in a model ELISA as described herein.

Portions and other variants of Ehrlichia antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In another aspect, the present invention provides antigenic epitopes of an Ehrlichia antigen or epitope repeat sequences, as well as polypeptides comprising at least two such contiguous antigenic epitopes. As used herein, an "epitope" is a portion of an antigen that reacts with sera from Ehrlichia-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise the amino acid sequence of SEQ ID NO: 30. As discussed in more detail below, antigenic epitopes provided herein may be employed in the diagnosis and treatment of Ehrlichia infection, either alone or in combination with other Ehrlichia antigens or antigenic epitopes. Antigenic epitopes and polypeptides comprising such epitopes may be prepared by synthetic means, as described generally above and in detail in Example 3.

In general, regardless of the method of preparation, the polypeptides and antigenic epitopes disclosed herein are prepared in substantially pure form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope, or an inventive polypeptide and an antigenic epitope of the present invention, together with variants of such fusion proteins. The fusion proteins of the present invention may also include a linker peptide between the polypeptides or antigenic epitopes.

A DNA sequence encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. An an alternative to the use of a peptide linker sequence (when desired), one can utilize non-essential N-terminal amino acid regions (when present) on the first and second polypeptides to separate the functional domains and prevent steric hindrance.

In another aspect, the present invention provides methods for using the polypeptides and antigenic epitopes described above to diagnose Ehrlichia infection, in particular HGE. In this aspect, methods are provided for detecting Ehrlichia infection in a biological sample, using one or more of the above polypeptides and antigenic epitopes, either alone or in combination. For clarity, the term "polypeptide" will be used when describing specific embodiments of the inventive diagnostic methods. However, it will be clear to one of skill in the art that the antigenic epitopes and fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Ehrlichia antigens which may be indicative of HGE.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with HGE. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies. A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, CA, and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Ehrlichia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for HGE. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for HGE.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Ehrlichia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

In yet another aspect, the present invention provides antibodies to the polypeptides and antigenic epitopes of the present invention. Antibodies may be prepared by any of a variety of techniques known to those of ordinary skill in the art. See, e.g, Harlow and Lane, *Antibodies: A Laboratory Manual*, Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide coupled to a suitable solid support.

Monoclonal antibodies specific for the antigenic polypeptide or epitope of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of Ehrlichia antigens using assays similar to those detailed above and other techniques well known to those of skill in the art, thereby providing a method for detecting Ehrlichia infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify Ehrlichia-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect Ehrlichia-specific sequences in biological samples. DNA probes or primers comprising oligonucleotide sequences described above may be used alone or in combination with each other.

In another aspect, the present invention provides methods for using one or more of the above polypeptides, antigenic epitopes or fusion proteins (or DNA molecules encoding such polypeptides) to induce protective immunity against Ehrlichia infection in a patient. As used herein, a "patient" refers to any warm-blooded animal, preferably a human. A patient may be afflicted with a disease, or may be free of detectable disease and/or infection. In other words, protective immunity may be induced to prevent or treat Ehrlichia infection, specifically HGE.

In this aspect, the polypeptide, antigenic epitope, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other Ehrlichia antigens, either incorporated into a combination polypeptide or present within a separate polypeptide.

Alternatively, a vaccine may contain DNA encoding one or more polypeptides, antigenic epitopes or fusion proteins as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g, vaccinia or other pox virus, retrovirus, or adenovirus), which may involve the use of a non-pathogenic (defective), virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known Ehrlichia antigen. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from HGE for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

The following Examples are offered by way of illustration and not by way of limitation.

EXAMPLE 1

ISOLATION OF DNA SEQUENCES ENCODING EHRLICHIA ANTIGENS

This example illustrates the preparation of DNA sequences encoding Ehrlichia antigens by screening an Ehrlichia genomic expression library, prepared using genomic DNA from the Ehrlichia species that is the causative agent of HGE, with sera obtained from mice infected with the HGE agent.

Ehrlichia genomic DNA was isolated from infected human HL60 cells and sheared by sonication. The resulting randomly sheared DNA was used to construct an Ehrlichia genomic expression library (approximately 0.5–4.0 kbp inserts) with EcoRI adaptors and a Lambda ZAP II/EcoRI/CIAP vector (Stratagene, La Jolla, Calif.). The unamplified library ($6.5\times10^6$/ml) was screened with an *E. coli* lysate-absorbed Ehrlichia mouse serum pool, as described in Sambrook et al., *Molecular Cloning: A Laboratory Manual*, Cold Spring Harbor Laboratories, Cold Spring Harbor, N.Y., 1989. Positive plaques were visualized and purified with goat-anti-mouse alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A (Foster City, Calif.).

Of the eighteen antigens isolated using this technique, seven (hereinafter referred to as HGE-1, HGE-3, HGE-6, HGE-7, HGE-12, HGE-23 and HGE-24) were found to be related. The determined DNA sequences for HGE-1, HGE-3, HGE-6, HGE-12, HGE-23 and HGE-24 are shown in SEQ ID NO: 1–3 and 5–7, respectively, with the 5' DNA sequence for HGE-7 being provided in SEQ ID NO: 4. The deduced amino acid sequences for HGE-1, HGE-3, HGE-6, HGE-7, HGE-12, HGE-23 and HGE-24 are provided in SEQ ID NO: 8–14, respectively. Comparison of these sequences with known sequences in the gene bank using the DNA STAR system, revealed some degree of homology to the Anaplasma marginale major surface protein.

Of the remaining eleven isolated antigens, no significant homologies were found to HGE-2, HGE-9, HGE-14, HGE-15, HGE-16, HGE-17, HGE-18 and HGE-25. The determined full-length DNA sequences for HGE-9 and HGE-14 are provided in SEQ ID NO: 16 and 17, respectively, with the determined 5' DNA sequences for HGE-2, HGE-15, HGE-16, HGE-17, HGE-18 and HGE-25 being shown in SEQ ID NO: 15, and 18–22, respectively. The corresponding predicted amino acid sequences for HGE-2, HGE-9, HGE-14 and HGE-18 are provided in SEQ ID NO: 23–26, respectively. The reverse complements of HGE-14, HGE-15 and HGE-18 were found to contain open reading frames which encode the amino acid sequences shown in SEQ ID NO: 27, 28 and 29, respectively. The predicted amino acid sequence from the reverse complement strand of HGE-14 (SEQ ID NO: 28) was found to contain a 41 amino acid repeat, provided in SEQ ID NO: 30.

The determined DNA sequence for the isolated antigen HGE-11 is provided in SEQ ID NO: 31, with the predicted amino acid sequences being provided in SEQ ID NO: 32 and 33. Comparison of these sequences with known sequence in the gene bank, revealed some homology between the amino acid sequence of SEQ ID NO: 32 and that of bacterial DNA-directed RNA polymerase beta subunit rpoB (Monastyrskaya, G.S. et al., 1990, *Bioorg. Khim.* 6:1106–1109), and further between the amino acid sequence of SEQ ID NO: 33 and that of bacterial DNA-directed RNA polymerase beta' subunit rpoC (Borodin A. M. et al, 1988 *Bioorg Khim.* 14:1179–1182).

The determined 5' DNA sequence for the antigen HGE-13 is provided in SEQ ID NO: 34. The opposite strand for HGE-13 was found to contain an open reading frame which encodes the amino acid sequence provided in SEQ ID NO: 35. This sequence was found to have some homology to bacterial 2,3-biphosphoglycerate-independent phosphoglycerate mutase (Leyva-Vazquez, M. A. and Setlow, P., 1994 *J. Bacteriol.* 176:3903–3910).

The determined partial nucleotide sequence for the isolated antigen GE-8 (SEQ ID NO: 36) was found to include, on the reverse complement of the 5' end, two open reading frames encoding the amino acid sequences provided in SEQ ID NO: 37 and 38. The amino acid sequences of SEQ ID NO: 37 and 38 were found to show some homology to prokaryotic and eukaryotic dihydrolipamide succinyltransferase (Fleischmann R. D. et al, 1995 *Science* 269:496–512) and methionine aminopeptidase (Chang, Y. H., 1992 *J Biol. Chem.* 267:8007–8011), respectively.

EXAMPLE 2

USE OF REPRESENTATIVE ANTIGENS FOR SERODIAGNOSIS OF HGE INFECTION

The diagnostic properties of representative Ehrlichia antigens were determined by Western blot analysis as follows. Antigens were induced as pBluescript SK—constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 1% BSA in 0.1% Tween 20™/PBS. Blots were then washed 3 times in 0.1% Tween 20™/PBS and incubated with either an HGE patient serum pool (1:200) or an Ehrlichia-infected mouse serum pool for a period of 2 hours. After washing in 0.1% Tween 20™/PBS 3 times, blots were incubated with a second antibody (goat-anti-human IgG conjugated to alkaline phosphatase (AP) or goat-anti-mouse IgG-AP, respectively) for 1 hour. Immunocomplexes were visualized with NBT/BCIP (Gibco BRL) after washing with Tween 20™/PBS three times and AP buffer (100 mM Tris-HCl, 100 mM Na Cl, 5 mM MgC$_2$, pH 9.5) two times.

As shown in FIG. 1, resulting bands of reactivity with serum antibody were seen at 37 kDa for HGE-1 and HGE-3 for both the mouse serum pool and the human serum pool. Protein size standards, in kDa (Gibco BRL, Gaithersburg, MB), are shown to the left of the blots.

Western blots were performed on partially purified HGE-1 and HGE-3 recombinant antigen with a series of patient sera from HGE patients, patients with Lyme disease, babesiosis patients or from normal donors. Specifically, purified antigen (4 μg) was separated by SDS-PAGE on 12% gels. Protein was then transferred to nitrocellulose membrane for immunoblot analysis. The membrane was first blocked with PBS containing 1% Tween 2™ for 2 hours. Membranes were then cut into strips and incubated with individual sera (1/500) for two hours. The strips were washed 3 times in PBS/0.1% Tween 2™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 2A:
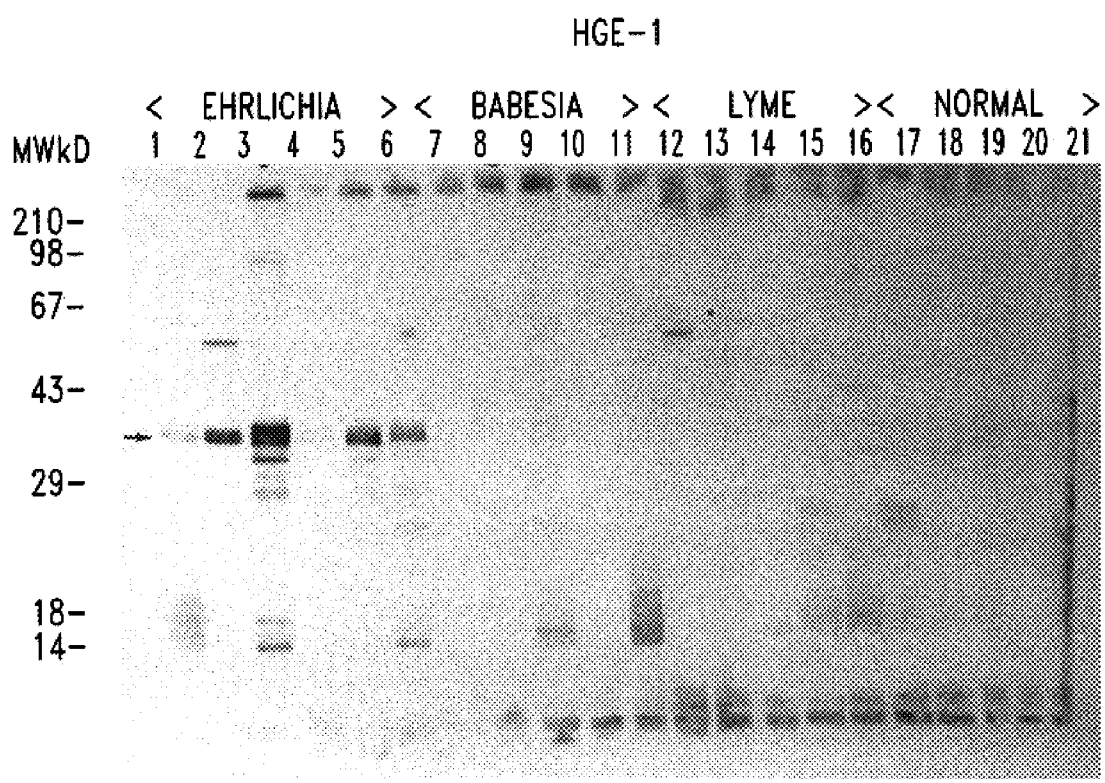
FIG. 2A and B show the reactivity of purified recombinant Ehrlichia antigens HGE-1 and HGE-3, respectively, with sera from HGE-infected patients, babesiosis-infected patients, Lyme-disease infected patients and normal donors as determined by Western blot analysis.
Figure 2B:
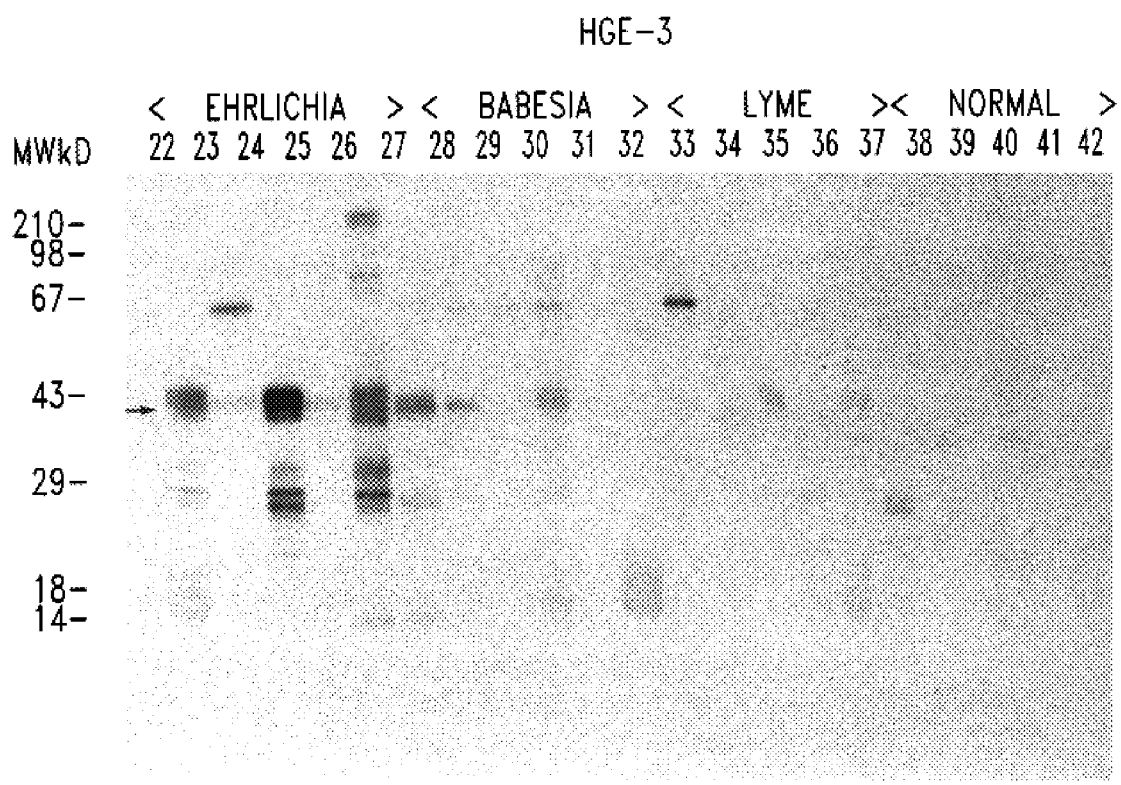

Lanes 1–6 of FIG. 2A show the reactivity of purified recombinant HGE-1 (MW 37 kD) with sera from six HGE-infected patients, of which all were clearly positive. In contrast, no immunoreactivity with HGE-1 was seen with sera from patients with either babesiosis (lanes 7–11), or Lyme disease (lanes 12–16), or with sera from normal individuals (lanes 17–21). As shown in FIG. 2B, HGE-3 (MW 37 kD) was found to react with sera from all six HGE patients (lanes 22–27), while cross-reactivity was seen with sera from two of the five babesiosis patients and weak cross-reactivity was seen with sera from two of the five Lyme disease patients. This apparent cross-reactivity may represent the ability of the antigen HGE-3 to detect low antibody titer in patients co-infected with HGE. No immunoreactivity of HGE-3 was seen with sera from normal patients.

EXAMPLE 3

SYNTHESIS OF SYNTHETIC POLYPEPTIDES

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising an Ehrlichia antigen, wherein said antigen comprises an amino acid sequence encoded by a DNA sequence selected from the group consisting of SEQ ID NO:2, the complements of said sequence, and DNA sequences that hybridize to SEQ ID NO:2 or a complement thereof under moderately stringent conditions.

2. A pharmaceutical composition comprising at least one polypeptide according to any one of claims 1 and 3 and a physiologically acceptable carrier.

3. An isolated polypeptide comprising an amino acid sequence of SEQ ID NO: 9.

* * * * *

UNITED STATES PATENT AND TRADEMARK OFFICE
CERTIFICATE OF CORRECTION

PATENT NO.    : 6,231,869 B1
DATED         : May 15, 2001
INVENTOR(S)   : Steven G. Reed et al.

It is certified that error appears in the above-identified patent and that said Letters Patent is hereby corrected as shown below:

<u>Title page,</u>
Item [54], title, "COMPOUNDS AND METHODS FOR THE DIAGNOSIS AND TREATMENT OF EHRLICHIA INFECTION" should read -- COMPOUNDS AND METHODS FOR THE DIAGNOSIS AND THERAPY OF EHRLICHIA INFECTION --.

Signed and Sealed this

Eighth Day of January, 2002

*Attest:*

*Attesting Officer*

JAMES E. ROGAN
*Director of the United States Patent and Trademark Office*

```
SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
        (A) LENGTH: 1345 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 1:

TTGAGCTTGA GATTGGTTAC GAGCGCTTCA AGACCAAGGG TATTAGAGAT AGTGGTAGTA        60

AGGAAGATGA AGCTGATACA GTATATCTAC TAGCTAAGGA GTTAGCTTAT GATGTTGTTA       120

CTGGTCAGAC TGATAACCTT GCCGCTGCTC TTGCCAAAAC CTCCGGTAAG GATATTGTTC       180

AGTTTGCTAA GGCGGTGGAG ATTTCTCATT CCGAGATTGA TGGCAAGGTT TGTAAGACGA       240

AGTCGGCGGG AACTGGAAAA AATCCGTGTG ATCATAGCCA AAAGCCGTGT AGTACGAATG       300
```

```
CGTATTATGC GAGGAGAACG CAGAAGAGTA GGAGTTCGGG AAAAACGTCT TTATGCGGGG      360

ACAGTGGGTA TAGCGGGCAG GAGCTAATAA CGGGTGGGCA TTATAGCAGT CCAAGCGTAT      420

TCCGGAATTT TGTCAAAGAC ACACTACAAG GAAATGGTAG TGAGAACTGG CCTACATCTA      480

CTGGAGAAGG AAGTGAGAGT AACGACAACG CCATAGCCGT TGCTAAGGAC CTAGTAAATG      540

AACTTACTCC TGAAGAACGA ACCATAGTGG CTGGGTTACT TGCTAAAATT ATTGAAGGAA      600

GCGAGGTTAT TGAGATTAGG GCCATCTCTT CGACTTCAGT TACAATGAAT ATTTGCTCAG      660

ATATCACGAT AAGTAATATC TTAATGCCGT ATGTTTGTGT TGGTCCAGGG ATGAGCTTTG      720

TTAGTGTTGT TGATGGTCAC ACTGCTGCAA AGTTTGCATA TCGGTTAAAG GCAGGTCTGA      780

GTTATAAATT TTCGAAAGAA GTTACAGCTT TTGCAGGTGT TTTTTACCAT CACGTTATAG      840

GAGATGGTGT TTATGATGAT CTGCCATTGC GGCATTTATC TGATGATATT AGTCCTGTGA      900

AACATGCTAA GGAAACCGCC ATTGCTAGAT TCGTCATGAG GTACTTTGGC GGGGAATTTG      960

GTGTTAGGCT CGCTTTTTAA GGTTGCGACC TAAAAGCACT TAGCTCGCCT TCACTCCCCC     1020

TTAAGCAATA TGATGCACAT TTGTTGCCCT ACAAATCTAA TATAAGGTTT GTTGCCTATA     1080

CTCGTGCCGA ATTCGGCACG AGGAGGAAGC TGAACTCACC CATCAGTCTC TCTCATCCGT     1140

TGGCCACCTG CTGTCCCCAC CCACCCACCA AACTGGTGCT TTTAATGGAA TCAGCTTTAA     1200

AAAGAAAAAA ATCCTCCAAG TAACAAAGCA CCCTATAATT ATTCCGCAGC TCCTTGTCCT     1260

CGGTAATTTT AGGCTTGTGC TGCTATCATT ACACATTACA TGGAGTTAGG GAGTCATAGC     1320

TCTTGTGTGG CCAATCAGTG ATACA                                          1345

(2) INFORMATION FOR SEQ ID NO: 2:

(i) SEQUENCE CHARACTERISTICS:
        (A) LENGTH: 1132 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 2:

ATTTCTATAT TGGTTTGGAT TACAGTCCAG CGTTTAGCAA GATAAGAGAT TTTAGTATAA       60

GGGAGAGTAA CGGAGAGACA AAGGCAGTAT ATCCATACTT AAAGGATGGA AAGAGTGTAA      120

AGCTAGAGTC ACACAAGTTT GACTGGAACA CACCTGATCC TCGGATTGGG TTTAAGGACA      180

ACATGCTTGT AGCTATGGAA GGTAGTGTTG GTTATGGTAT TGGTGGTGCC AGGGTTGAGC      240

TTGAGATTGG TTACGAGCGC TTCAAGACCA AGGGTATTAG AGATAGTGGT AGTAAGGAAG      300

ATGAAGCTGA TACAGTATAT CTACTAGCTA AGGAGTTAGC TTATGATGTT GTTACTGGAC      360

AGACTGATAA CCTTGCTGCT GCTCTTGCTA AGACCTCGGG GAAAGACATC GTTCAGTTTG      420

CTAAGGCGGT TGGGGTTTCT CATCCTAGTA TTGATGGGAA GGTTTGTAAG ACGAAGGCGG      480

ATAGCTCGAA GAAATTTCCG TTATATAGTG ACGAAACGCA CACGAAGGGG GCAAATGAGG      540

GGAGAACGTC TTTGTGCGGT GACAATGGTA GTTCTACGAT AACAACCAGT GGTACGAATG      600

TAAGTGAAAC TGGGCAGGTT TTTAGGGATT TTATCAGGGC AACGCTGAAA GAGGATGGTA      660

GTAAAAACTG GCCAATTTCA AGCGGCACGG GAACTCCAAA ACCTGTCACG AACGACAACG      720

CCAAAGCCGT AGGTAAAGAC CTAGTACAGG AGCTAACCCC TGAAGAAAAA ACCATAGTAG      780
```

```
CAGGGTTACT AGCTAAGACT ATTGAAGGGG GTGAAGTTGT TGAGATCAGG GCGGTTTCTT      840

CTACTTCCGT AATGGTCAAT GCTTGTTATG ATCTTCTTAG TGAAGGTTTA GGTGTTGTTC      900

CTTATGCTTG TGTTGGTCTC GGTGGTAACT TCGTGGGCGT GGTTGATGGA ATTCATTACA      960

CAAACCATCT TTAACTCTGA ATACCCTAGT TAAGGTAAGT GAAGTAACTA GGCAAATTAG     1020

TGCTGCACCA CTCGTGAAAC AAACTACGAT CAGCGATTCA CCATACTTAG TAGGTCCGTA     1080

CAGTGGCTTT ACGCTCTTAC CCATCATGAA AAATACTTGC TATCTAGGAA TC            1132
```

(2) INFORMATION FOR SEQ ID NO: 3:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 3:

```
CTACTAGCTA AGGAGTTAGC TTATGATGTT GTTACTGGGC AGACTGATAA CCTTGCTGCT       60

GCTCTTGCCA AGACTTCTGG TAAAGATATT GTTCAGTTTG CTAAGACTCT TAATATTTCT      120

CACTCTAATA TCGATGGGAA GGTTTGTAGG AGGGAAAAGC ATGGGAGTCA AGGTTTGACT      180

GGAACCAAAG CAGGTTCGTG TGATAGTCAG CCACAAACGG CGGGTTTCGA TTCCATGAAA      240

CAAGGTTTGA TGGCAGCTTT AGGCGAACAA GGCGCTGAAA AGTGGCCCAA AATTAACAAT      300

GGTGGCCACG CAACAATTTA TAGTAGTAGC GCAGGTCCAG GAAATGCGTA TGCTAGAGAT      360

GCATCTACTA CGGTAGCTAC AGACCTAACA AAGCTCACTA CTGAAGAAAA AACCATAGTA      420

GCAGGGTTAC TAGCTAGAAC TATTGAAGGG GGTGAAGTTG TTGAGATTAG GGCAGTTTCT      480

TCTACTTCTG TGATGGTTAA TGCTTGTTAT GATCTTCTTA GTGAAGGTTT AGGTGTTGTA      540

CCTTATGCTT GTGT                                                        554
```

(2) INFORMATION FOR SEQ ID NO: 4:

(i) SEQUENCE CHARACTERISTICS:
        (A) LENGTH: 559 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 4:

```
ATGCTGTGAA AATTACTAAC TCCACTATCG ATGGGAAGGT TTGTAATGGT AGTAGAGAGA       60

AGGGAATAG TGCTGGGAAC AACAACAGTG CTGTGGCTAC CTACGCGCAG ACTCACACAG       120

CGAATACATC AACGTCACAG TGTAGCGGTC TAGGGACCAC TGTTGTCAAA CAAGGTTATG      180

GAAGTTTGAA TAAGTTTGTT AGCCTGACGG GGGTTGGTGA AGGTAAAAAT TGGCCTACAG      240

GTAAGATACA CGACGGTAGT AGTGGTGTCA AAGATGGTGA ACAGAACGGG AATGCCAAAG      300

CCGTAGCTAA AGACCTAGTA GATCTTAATC GTGACGAAAA AACCATAGTA GCAGGATTAC      360

TAGCTAAAAC TATTGAAGGG GGTGAAGTTG TTGAGATCAG GGCGGTTTCT TCTACTTCTG      420

TGATGGTTAA TGCTTGTTAT GATCTTCTTA GTGAAGGTTT AGGCGTTGTT CCTTACGCTT      480
```

```
GTGTCGGTCT CGGAGGTAAC TTCGTGGGCG TTGTTGATGG GCATATCACT CCTAAGCTTG      540

CTTATAGATT AAAGGCTGG                                                  559
```

(2) INFORMATION FOR SEQ ID NO: 5:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 5:

```
AGCGCTTCAA GACCAAGGGT ATTAGAGATA GTGGTAGTAA GGAAGATGAA GCTGATACAG       60

TATATCTACT AGCTAAGGAG TTAGCTTATG ATGTTGTTAC TGGACAGACT GATAACCTTG      120

CCGCTGCTCT TGCTAAAACC TCGGGGAAAG ACTTTGTTCA GTTTGCTAAG GCCGTGGAGA      180

TTTCTAATTC TACGATTGGG G                                               201
```

(2) INFORMATION FOR SEQ ID NO: 6:

(i) SEQUENCE CHARACTERISTICS:
        (A) LENGTH: 467 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 6:

```
GGTATATCGA TAGCCTACGT AGTCACTCCT TATTATTAAA AAGGAAGACC AAGGGTATTA       60

GAGATAGTGG AAGTAAGGAA GATGAAGCAG ATACAGTATA TCTACTAGCT AAGGAGTTAG      120

CTTATGATGT TGTTACTGGG CAGACTGATA ACCTTGCCGC TGCTCTTGCC AAAACCTCCG      180

GTAAGGACTT TGTTAAATTT GCCAATGCTG TTGTTGGAAT TTCTCACCCC GATGTTAATA      240

AGAAGGTTTG TGCGACGAGG AAGGACAGTG GTGGTACTAG ATATGCGAAG TATGCTGCCA      300

CGACTAATAA GAGCAGCAAC CCTGAAACCT CACTGTGTGG AGACGAAGGT GGCTCGAGCG      360

GCACGAATAA TACACAAGAG TTTCTTAAGG AATTTGTAGC CCAAACCCTA GTAGAAAATG      420

AAAGTAAAAA CTGGCCTACT TCAAGCGGGA CTGGGTTGAA GACTAAC                   467
```

(2) INFORMATION FOR SEQ ID NO: 7:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 7:

```
AAGATGAAGC TGATACAGTA TATCTACTGG CTAAGGAGTT AGCTTATGAT GTTGTTACTG       60
```

```
GACAGACTGA TAAGCTTACT GCTGCTCTTG CTAAGACCTC CGGGAAGGAC TTTGTTCAGT    120

TTGCTAAGGC GGTTGGGGTT TCTCATCCTA ATATCGATGG GAAGGTTTGT AAGACTACGC    180

TAGGGCACAC GAGTGCGGAT AGCTACGGTG TGTATGGGGA GTTAACAGGC CAGGCGAGTG    240

CGAGTGAGAC ATCGTTATGT GGTGGTAAGG GTAAAAATAG TAGTGGTGGT GGAGCTGCTC    300

CCGAAGTTTT AAGGGACTTT GTAAAGAAAT CTCTGAAAGA TGGGGGCCAA AACTGGCCAA    360

CATCTAGGGC GACCGAGAGT TCACCTAAGA CTAAATCTGA AACTAACGAC AATGCAAAAG    420

CTGTCGCTAA AGACCTAGTA GACCTTAATC CTGAAGAAAA AACCATAGTA GCAGGGTTAC    480

TAGCTAAAAC TATTGAAGGT GGGGAAGTTG TAGAAATCAG AGCAGTTTCT               530
```

(2) INFORMATION FOR SEQ ID NO: 8:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 8:

```
Glu Leu Glu Ile Gly Tyr Glu Arg Phe Lys Thr Lys Gly Ile Arg Asp
1               5                   10                  15

Ser Gly Ser Lys Glu Asp Glu Ala Asp Thr Val Tyr Leu Leu Ala Lys
            20                  25                  30

Glu Leu Ala Tyr Asp Val Val Thr Gly Gln Thr Asp Asn Leu Ala Ala
        35                  40                  45

Ala Leu Ala Lys Thr Ser Gly Lys Asp Ile Val Gln Phe Ala Lys Ala
    50                  55                  60

Val Glu Ile Ser His Ser Glu Ile Asp Gly Lys Val Cys Lys Thr Lys
65                  70                  75                  80

Ser Ala Gly Thr Gly Lys Asn Pro Cys Asp His Ser Gln Lys Pro Cys
                85                  90                  95

Ser Thr Asn Ala Tyr Tyr Ala Arg Arg Thr Gln Lys Ser Arg Ser Ser
            100                 105                 110

Gly Lys Thr Ser Leu Cys Gly Asp Ser Gly Tyr Ser Gly Gln Glu Leu
        115                 120                 125

Ile Thr Gly Gly His Tyr Ser Ser Pro Ser Val Phe Arg Asn Phe Val
    130                 135                 140

Lys Asp Thr Leu Gln Gly Asn Gly Ser Glu Asn Trp Pro Thr Ser Thr
145                 150                 155                 160

Gly Glu Gly Ser Glu Ser Asn Asp Asn Ala Ile Ala Val Ala Lys Asp
                165                 170                 175

Leu Val Asn Glu Leu Thr Pro Glu Glu Arg Thr Ile Val Ala Gly Leu
            180                 185                 190

Leu Ala Lys Ile Ile Glu Gly Ser Glu Val Ile Glu Ile Arg Ala Ile
        195                 200                 205

Ser Ser Thr Ser Val Thr Met Asn Ile Cys Ser Asp Ile Thr Ile Ser
    210                 215                 220

Asn Ile Leu Met Pro Tyr Val Cys Val Gly Pro Gly Met Ser Phe Val
225                 230                 235                 240

Ser Val Val Asp Gly His Thr Ala Ala Lys Phe Ala Tyr Arg Leu Lys
                245                 250                 255
```

```
Ala Gly Leu Ser Tyr Lys Phe Ser Lys Glu Val Thr Ala Phe Ala Gly
            260                 265                 270

Gly Phe Tyr His His Val Ile Gly Asp Gly Val Tyr Asp Asp Leu Pro
        275                 280                 285

Leu Arg His Leu Ser Asp Asp Ile Ser Pro Val Lys His Ala Lys Glu
    290                 295                 300

Thr Ala Ile Ala Arg Phe Val Met Arg Tyr Phe Gly Gly Glu Phe Gly
305                 310                 315                 320

Val Arg Leu Ala Phe
                325

(2) INFORMATION FOR SEQ ID NO: 9:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 9:

Phe Tyr Ile Gly Leu Asp Tyr Ser Pro Ala Phe Ser Lys Ile Arg Asp
1               5                   10                  15

Phe Ser Ile Arg Glu Ser Asn Gly Glu Thr Lys Ala Val Tyr Pro Tyr
                20                  25                  30

Leu Lys Asp Gly Lys Ser Val Lys Leu Glu Ser His Lys Phe Asp Trp
            35                  40                  45

Asn Thr Pro Asp Pro Arg Ile Gly Phe Lys Asp Asn Met Leu Val Ala
        50                  55                  60

Met Glu Gly Ser Val Gly Tyr Gly Ile Gly Gly Ala Arg Val Glu Leu
65                  70                  75                  80

Glu Ile Gly Tyr Glu Arg Phe Lys Thr Lys Gly Ile Arg Asp Ser Gly
                85                  90                  95

Ser Lys Glu Asp Glu Ala Asp Thr Val Tyr Leu Leu Ala Lys Glu Leu
            100                 105                 110

Ala Tyr Asp Val Val Thr Gly Gln Thr Asp Asn Leu Ala Ala Ala Leu
        115                 120                 125

Ala Lys Thr Ser Gly Lys Asp Ile Val Gln Phe Ala Lys Ala Val Gly
    130                 135                 140

Val Ser His Pro Ser Ile Asp Gly Lys Val Cys Lys Thr Lys Ala Asp
145                 150                 155                 160

Ser Ser Lys Lys Phe Pro Leu Tyr Ser Asp Glu Thr His Thr Lys Gly
                165                 170                 175

Ala Asn Glu Gly Arg Thr Ser Leu Cys Gly Asp Asn Gly Ser Ser Thr
            180                 185                 190

Ile Thr Thr Ser Gly Thr Asn Val Ser Glu Thr Gly Gln Val Phe Arg
        195                 200                 205

Asp Phe Ile Arg Ala Thr Leu Lys Glu Asp Gly Ser Lys Asn Trp Pro
    210                 215                 220

Ile Ser Ser Gly Thr Gly Thr Pro Lys Pro Val Thr Asn Asp Asn Ala
225                 230                 235                 240

Lys Ala Val Gly Lys Asp Leu Val Gln Glu Leu Thr Pro Glu Glu Lys
                245                 250                 255
```

```
Thr Ile Val Ala Gly Leu Leu Ala Lys Thr Ile Glu Gly Gly Glu Val
            260                 265                 270

Val Glu Ile Arg Ala Val Ser Ser Thr Ser Val Met Val Asn Ala Cys
            275                 280                 285

Tyr Asp Leu Leu Ser Glu Gly Leu Gly Val Val Pro Tyr Ala Cys Val
            290                 295                 300

Gly Leu Gly Gly Asn Phe Val Gly Val Val Asp Gly Ile His Tyr Thr
305                 310                 315                 320

Asn His Leu (2) INFORMATION FOR SEQ ID NO: 10:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 10:

Leu Leu Ala Lys Glu Leu Ala Tyr Asp Val Val Thr Gly Gln Thr Asp
1               5                   10                  15

Asn Leu Ala Ala Ala Leu Ala Lys Thr Ser Gly Lys Asp Ile Val Gln
            20                  25                  30

Phe Ala Lys Thr Leu Asn Ile Ser His Ser Asn Ile Asp Gly Lys Val
            35                  40                  45

Cys Arg Arg Glu Lys His Gly Ser Gln Gly Leu Thr Gly Thr Lys Ala
50                  55                  60

Gly Ser Cys Asp Ser Gln Pro Gln Thr Ala Gly Phe Asp Ser Met Lys
65                  70                  75                  80

Gln Gly Leu Met Ala Ala Leu Gly Glu Gln Gly Ala Glu Lys Trp Pro
            85                  90                  95

Lys Ile Asn Asn Gly Gly His Ala Thr Ile Tyr Ser Ser Ser Ala Gly
            100                 105                 110

Pro Gly Asn Ala Tyr Ala Arg Asp Ala Ser Thr Thr Val Ala Thr Asp
            115                 120                 125

Leu Thr Lys Leu Thr Thr Glu Glu Lys Thr Ile Val Ala Gly Leu Leu
            130                 135                 140

Ala Arg Thr Ile Glu Gly Gly Glu Val Val Glu Ile Arg Ala Val Ser
145                 150                 155                 160

Ser Thr Ser Val Met Val Asn Ala Cys Tyr Asp Leu Leu Ser Glu Gly
            165                 170                 175

Leu Gly Val Val Pro Tyr Ala Cys Val
            180                 185

(2) INFORMATION FOR SEQ ID NO: 11:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (vi) ORIGINAL SOURCE:
```

(A) ORGANISM: Ehrlichia (xi) SEQUENCE DESCRIPTION: SEQ ID NO: 11:

Ala Val Lys Ile Thr Asn Ser Thr Ile Asp Gly Lys Val Cys Asn Gly
1               5                   10                  15

Ser Arg Glu Lys Gly Asn Ser Ala Gly Asn Asn Ser Ala Val Ala
            20                  25                  30

Thr Tyr Ala Gln Thr His Thr Ala Asn Thr Ser Thr Ser Gln Cys Ser
        35                  40                  45

Gly Leu Gly Thr Thr Val Val Lys Gln Gly Tyr Gly Ser Leu Asn Lys
        50                  55                  60

Phe Val Ser Leu Thr Gly Val Gly Glu Gly Lys Asn Trp Pro Thr Gly
65                  70                  75                  80

Lys Ile His Asp Gly Ser Ser Gly Val Lys Asp Gly Glu Gln Asn Gly
                85                  90                  95

Asn Ala Lys Ala Val Ala Lys Asp Leu Val Asp Leu Asn Arg Asp Glu
            100                 105                 110

Lys Thr Ile Val Ala Gly Leu Leu Ala Lys Thr Ile Glu Gly Gly Glu
            115                 120                 125

Val Val Glu Ile Arg Ala Val Ser Ser Thr Ser Val Met Val Asn Ala
130                 135                 140

Cys Tyr Asp Leu Leu Ser Glu Gly Leu Gly Val Val Pro Tyr Ala Cys
145                 150                 155                 160

Val Gly Leu Gly Gly Asn Phe Val Gly Val Val Asp Gly His Ile Thr
                165                 170                 175

Pro Lys Leu Ala Tyr Arg Leu Lys Ala
            180                 185

(2) INFORMATION FOR SEQ ID NO: 12:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 12:

Arg Phe Lys Thr Lys Gly Ile Arg Asp Ser Gly Ser Lys Glu Asp Glu
1               5                   10                  15

Ala Asp Thr Val Tyr Leu Leu Ala Lys Glu Leu Ala Tyr Asp Val Val
            20                  25                  30

Thr Gly Gln Thr Asp Asn Leu Ala Ala Ala Leu Ala Lys Thr Ser Gly
        35                  40                  45

Lys Asp Phe Val Gln Phe Ala Lys Ala Val Glu Ile Ser Asn Ser Thr
        50                  55                  60

Ile Gly
65

(2) INFORMATION FOR SEQ ID NO: 13:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: Ehrlichia (xi) SEQUENCE DESCRIPTION: SEQ ID NO: 13:

```
Tyr Ile Asp Ser Leu Arg Ser His Ser Leu Leu Lys Arg Lys Thr
1               5                   10                  15

Lys Gly Ile Arg Asp Ser Gly Ser Lys Glu Asp Glu Ala Asp Thr Val
            20                  25                  30

Tyr Leu Leu Ala Lys Glu Leu Ala Tyr Asp Val Val Thr Gly Gln Thr
                35                  40                  45

Asn Leu Ala Ala Ala Leu Ala Lys Thr Ser Gly Lys Asp Phe Val
50                      55                  60

Lys Phe Ala Asn Ala Val Val Gly Ile Ser His Pro Asp Val Asn Lys
65                  70                  75                  80

Lys Val Cys Ala Thr Arg Lys Asp Ser Gly Gly Thr Arg Tyr Ala Lys
                85                  90                  95

Tyr Ala Ala Thr Thr Asn Lys Ser Ser Asn Pro Glu Thr Ser Leu Cys
                100                 105                 110

Gly Asp Glu Gly Gly Ser Ser Gly Thr Asn Asn Thr Gln Glu Phe Leu
                115                 120                 125

Lys Glu Phe Val Ala Gln Thr Leu Val Glu Asn Glu Ser Lys Asn Trp
                130                 135                 140

Pro Thr Ser Ser Gly Thr Gly Leu Lys Thr Asn
145                 150                 155
```

(2) INFORMATION FOR SEQ ID NO: 14:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 14:

```
Asp Glu Ala Asp Thr Val Tyr Leu Leu Ala Lys Glu Leu Ala Tyr Asp
1               5                   10                  15

Val Val Thr Gly Gln Thr Asp Lys Leu Thr Ala Ala Leu Ala Lys Thr
            20                  25                  30

Ser Gly Lys Asp Phe Val Gln Phe Ala Lys Ala Val Gly Val Ser His
                35                  40                  45

Pro Asn Ile Asp Gly Lys Val Cys Lys Thr Thr Leu Gly His Thr Ser
50                  55                  60

Ala Asp Ser Tyr Gly Val Tyr Gly Glu Leu Thr Gly Gln Ala Ser Ala
65                  70                  75                  80

Ser Glu Thr Ser Leu Cys Gly Gly Lys Gly Lys Asn Ser Ser Gly Gly
                85                  90                  95

Gly Ala Ala Pro Glu Val Leu Arg Asp Phe Val Lys Lys Ser Leu Lys
                100                 105                 110

Asp Gly Gly Gln Asn Trp Pro Thr Ser Arg Ala Thr Glu Ser Ser Pro
                115                 120                 125

Lys Thr Lys Ser Glu Thr Asn Asp Asn Ala Lys Ala Val Ala Lys Asp
```

```
            130                 135                 140
Leu Val Asp Leu Asn Pro Glu Glu Lys Thr Ile Val Ala Gly Leu Leu
145                 150                 155                 160

Ala Lys Thr Ile Glu Gly Gly Glu Val Val Glu Ile Arg Ala Val Ser
                165                 170                 175
```

(2) INFORMATION FOR SEQ ID NO: 15:

(i) SEQUENCE CHARACTERISTICS:
        (A) LENGTH: 1185 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 15:

```
GAAACAGCAT TGCTAGATTT CGTTGAACAA TTTGCTAATT TGCAACTAAA GCACTCATGA    60
TAAAGCTTGA TAGTATTTTA GAGGATAGTA GGCAATATGG TTTAGGGGAT TTCTTCGCAT   120
ACTTGTTATC ATCGTCCTTA TTTGTGCTTA GTTGGTCGGA TATTTGTGCA AGTTGTTGTA   180
AAATATGCAT ATTGTATGTA TAGGTGTGCA AGATATCATC TCTTTAGGTG TATCGTGTAG   240
CACTTAAACA AATGCTGGTG AACGTAGAGG GATTAAAGGA GGATTTGCGT ATATGTATGG   300
TATAGATATA GAGCTAAGTG ATTACAGAAT TGGTAGTGAA ACCATTTCCA GTGGAGATGA   360
TGGCTACTAC GAAGGATGTG CTTGTGACAA AGATGCCAGC ACTAATGCGT ACTCGTATGA   420
CAAGTGTAGG GTAGTACGGG GAACGTGGAG ACCGAGCGAA CTGGTTTTAT ATGTTGGTGA   480
TGAGCATGTG GCATGTAGAG ATGTTGCTTC GGGTATGCAT CATGGTAATT TGCCAGGGGA   540
AGGTGTATTT TATAGAGGCA GAAGCGGGCA GAGCTGCTAC TGCTGAAGGT GGTGTTTATA   600
CTACCGTTGT GGAGGCATTA TCGCTGGTGC AAGAGGAAGA GGGTACAGGT ATGTACTTGA   660
TAAACGCACC AGAAAAAGCG GTCGTAAGGT TTTTCAAGAT AGAAAAGAGT GCAGCAGAGG   720
AACCTCAAAC AGTAGATCCT AGTGTAGTTG AGTCAGCAAC AGGGTCGGGT GTAGATACGC   780
AAGAAGAACA AGAAATAGAT CAAGAAGCAC CAGCAATTGA AGAAGTTGAG ACAGAAGAGC   840
AAGAAGTTAT TCTGGAAGAA GGTACTTTGA TAGATCTTGA GCAACCTGTA GCGCAAGTAC   900
CTGTAGTAGC TGAAGCAGAA TTACCTGGTG TTGAAGCTGC AGAAGCGATT GTACCATCAC   960
TAGAAGAAAA TAAGCTTCAA GAAGTGGTAG TTGCTCCAGA AGCGCAACAA CTAGAATCAG  1020
CTCCTGAAGT TTCTGCGCCA GCACAACCTG AGTCTACAGT TCTTGGTGTT GCTGAAGGTG  1080
ATCTAAAGTC TGAAGTATCT GTAGAAGCTA ATGCTGATGT ACGCAAAAAG AAGTAATCTC  1140
TGGTCCACRA GAGCAAGAAA TTGCAGAAGC ACTAGAGGGA ACTGA               1185
```

(2) INFORMATION FOR SEQ ID NO: 16:

(i) SEQUENCE CHARACTERISTICS:
        (A) LENGTH: 1131 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 16:

-continued

```
ATAAAGGGGC TCCAGCAACG CAGAGAGATG CTTATGGTAA GACGGCTTTA CATATAGCAG      60

CTGCTAATGG TGACGGTAAG CTATATAAGT TAATTGCGAA AAAATGCCCA GATAGCTGTC     120

AAGCACTCCT TTCTCATATG GGAGATACAG CGTTACATGA GGCTTTATAT TCTGATAAGG    180

TTACAGAAAA ATGCTTTTTA AAGATGCTTA AAGAGTCTCG AAAGCATTTG TCAAACTCAT    240

CTTTCGGAGA CTTGCTTAAT ACTCCTCAAG AAGCAAATGG TGACACGTTA CTGCATCTGG    300

CTGCATCGCG TGGTTTCGGT AAAGCATGTA AAATACTACT AAAGTCTGGG GCGTCAGTAT    360

CAGTCGTGAA TGTAGAGGGA AAAACACCGG TAGATGTTGC GGATCCATCA TTGAAAACTC    420

GTCCGTGGTT TTTTGGAAAG TCCGTTGTCA CAATGATGGC TGAACGTGTT CAAGTTCCTG    480

AAGGGGGATT CCCACCATAT CTGCCGCCTG AAAGTCCAAC TCCTTCTTTA GGATCTATTT    540

CAAGTTTTGA GAGTGTCTCT GCGCTATCAT CCTTGGGTAG TGGCCTAGAT ACTGCAGGAG    600

CTGAGGAGTC TATCTACGAA GAAATTAAGG ATACAGCAAA AGGTACAACG GAAGTTGAAA    660

GCACATATAC AACTGTAGGA GCTGAGGAGT CTATCTACGA AGAAATTAAG GATACAGCAA    720

AAGGTACAAC GGAAGTTGAA AGCACATATA CAACTGTAGG AGCTGAAGGT CCGAGAACAC    780

CAGAAGGTGA AGATCTGTAT GCTACTGTGG GAGCTGCAAT TACTTCCGAG GCGCAAGCAT    840

CAGATGCGGC GTCATCTAAG GGAGAAAGGC CGGAATCCAT TTATGCTGAT CCATTTGATA    900

TAGTGAAACC TAGGCAGGAA AGGCCTGAAT CTATCTATGC TGACCCATTT GCTGCGGAAC    960

GAACATCTTC TGGAGTAACG ACATTTGGCC CTAAGGAAGA GCCGATTTAT GCAACAGTGA   1020

AAAAGGGTCC TAAGAAGAGT GATACTTCTC AAAAAGAAGG AACAGCTTCT GAAAAAGTCG   1080

GCTCAACAAT AACTGTGATT AAGAAGAAAG TGAAACCTCA GGTTCCAGCT A            1131
```

(2) INFORMATION FOR SEQ ID NO: 17:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 17:

```
AATGCGCTCC ACATAACTAG CATAACGTTT TCAGCAACGG CAGATCTTCA TATATAAGCA     60

CTGAACACCT ACGTTCCAAG ATCATGCTCT TCGCGCCTGT TTACTTGGTG GCTCAGAGTC    120

ATCATCACTA GGAGTTCGTG GTCTGTGAGA GCTAACTTGT GCTTCTTCCA GCGTATAACT    180

AGCACCTCCC AATCCTGATG CTGAAGGTTG ATCCCACGAA TAAGGCATAA TCCCTTGATC    240

CTGAGGTGGC ACATAGGGAG CTTGTGATCT TCCCATTCCA GTACTAGTAC CTCCTAGCCC    300

AGATGTTGAG AATTGGCTAG ATGGATAAGG AACATTCTCT AGGACACGTA GTATAATATG    360

AGGGGGGGGG GGAACGAGTT GAGCTCCCTG TCCGGCAGTA CCTCCCAATC CTGATGTTGA    420

GGGTTGATCC CATGATGTTG AGGGTTGATC CCACGATGTT GAAGGTTGTG CATACGAATA    480

GGGCATCATC CCTGGATCAT GTGGTGGAAT ATGCGAAGCT TGTTGACTTC CCATTCCAGC    540

GGCACTTCCT AACCCTGATG TTGAGGGTTG ATCCCACGAT GTTGAATGTT GTGCATACGA    600

ATAGGGCATC ATCCCTGGAT CATGTGGTGG AATATGCGAA GCTTGTTGAC TTCCCATTCC    660

AGCGGCACTT CCTAACCCTG ATGTTGAGGG TTGATCCCAC GATGTTGAAG GTTGTGCATA    720
```

-continued

CGAATAGGGC ATCATCCCTG GATCATGTGG TGGAATATGC GAAGCTTGTT GACTTCCCGT 780

TCCAGCGGCA CTTCCTAACC 800

(2) INFORMATION FOR SEQ ID NO: 18:

(i) SEQUENCE CHARACTERISTICS:
(A) LENGTH: 1011 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Ehrlichia (xi) SEQUENCE DESCRIPTION: SEQ ID NO: 18:

AATGTATACA GTCTCAGATT CAGAATCTAT AACTTCTTTC GTTACTCCAC CAATGTTAAT 60

GGCGAATATC TCATCGACTA AGCGTTCAGG ATACTTGCTA TCATTGTCGG TAGAGCCATC 120

TGACTTTTTT ACCGTGACAT TCTTTTTAAA AGAAACTCCA TTTACAACGG ACAATTCAGT 180

GCCATTTTGT AGCTTCGAGC GCAACTCCAC AGCAAATTCA CGTATTTTCT TCATACGTAA 240

TGCACTCTTC CATTCTTCAG TAAGAATAGA CCTGCTTTCT TCAAGTGTCC TTGGTCTTGG 300

AGGCACTACT TCAGTAACAA GAACGCCGAA ATAAGCGTCA CCATTGCTAA CCAGATGAGA 360

CGGTTTTCCT ACGGCAGATG AAAACGCCAA AGTAGTAAAG GCGTTTATAC CAAGCTGCAA 420

CGGAAAGTCT TTCACTAAGT TGCCAGATTT ATCGAGCCCA TGCATATCAA AATTCGTCAA 480

AACACCACTG ATCCGCGCAC CAAACATATC CTTTAGTTCA TTCAGCAATG CCCCGCGGCT 540

GATCATATCG TTTGCTTTTT TCACATTGCT AACTAGCAAC TCACCTGCCT TTTGCCTTCT 600

AATATTTGAA GATATCTTCT CTTTCAGCTT TTCTAGGTCT TCCTTAGTGA TCTCATGCTT 660

CCTTATTACC TTCATGATAT GCCAGCCGAC AACGCTACGG AACATTTCAC TGACTTCTCC 720

TTCATTTAGT GCAAACACCA CATTTCGCAC ACCTACCGGA AGAACATCCT TAGAGATATT 780

ATTGAGTGCA ATATCCTCTA TGGTGTAGCC AGCATCACTA ACCAATTCCT CAAAAGACTT 840

ACCCTCTTGG TAAGCTTTGT AAGCTAGCTC AGCTTCATTT TTGTCTGTAA ATACTAAATT 900

TAGAACATCT CTTTGATCAT GTAGTTCACT GTTTTTAATC TCAACGTCTA CCTTCTTGAT 960

CCGAAACAAT GACATCAGCA AGCAAGTCGT CTTCTGCCAT GATTATATGA T 1011

(2) INFORMATION FOR SEQ ID NO: 19:

(i) SEQUENCE CHARACTERISTICS:
(A) LENGTH: 513 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Ehrlichia (xi) SEQUENCE DESCRIPTION: SEQ ID NO: 19:

GCAAATATTT TTCTTGGTGC CGCCCTAAAA GCCTGAAAAA TTTAAAGAAA TGTTACTGCT 60

CTAGTCATTC ATAAAATGCA AATAGCCTAC AGAAGGAGTA TTTACTGCTA TAGGCTTGAA 120

AGTGCAATCG TTATTTACTA TTTTTTATAC ATATCGCAGT ACAGAGATTT TACGCGCTAC 180

GCCTGTGCAT CATAGCCGTA TTGCATCAAT AAATTGTCGT TGCTACGCGG GAAAGCTGCT 240

TAGCGCTTGA CCATTTTTCA TACACATTGT ACCATCATAG CGAGTGTGGT GCTCATGAGA 300

```
GTGCGTAGTG TTGCCGCCGG TTTCTCATGT TATAATCTTG CTGCCGTTTT GTGCAGAAGG      360

AGGAGTAGTC TCGTTTTTTT CCAAAAGACA ATGTGCTGGA GTGTCCCGGT GAGCCTCAAG      420

GTTCTTGTGG GATTTGTGTG GGCTGTTGTA TAAATACCAC GTTCGAAGCT GTCCTAGTGT      480

ATTCAGCATA TGTTGAGGAA GTTGTTGCTA TGA                                   513

(2) INFORMATION FOR SEQ ID NO: 20:

(i) SEQUENCE CHARACTERISTICS:
        (A) LENGTH: 464 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 20:

AGTCATTGAG TCGAGGGTAG TCTTGTGGAT CCCTGATAAA TGTTCTAAAA TTTAAAACAA       60

CACTAGAGTT TTGATCACAT GTTGGTTGTC AGAAAAAAAA TGTCAAAAAA TTTACCAGGG      120

CTTTTTGAAA TGCCTAGATT TTCCATTTCT CAATGAAACT TGTTTGATCA TGACTATTCC      180

AGCTAATGGA GCAGTGTGAT GTAGAGGAAG GAGCCACTGA GGGTATGTGG GGTGTTAGAC      240

TGGATCATCA TTCTTCAAGG CGTGTTCCTT GGAATGCCTG GGAGGAGAGC AATTTTCTAT      300

TAAAATTTAA TTCGCCTCCT TCCAAATATG GTTCCCTGGA CGATTTAGCA AATAGCATTC      360

CTTTTTTGGA GATTCAAAAA GCACATTAGC ATTGAGGATT GCTACAGTAA AGAAATCTGC      420

CTAACTTTGT TTTATCCAGT ATTGCCTAAA ATTATTGGAC CACT                      464

(2) INFORMATION FOR SEQ ID NO: 21:

(i) SEQUENCE CHARACTERISTICS:
        (A) LENGTH: 527 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 21:

CCTATGGCAG CTCTAAACTC GGCACGACTG GTTTCTACAA GAGATTGGTC GACATTAAAC       60

CATGCGAAAT CATTGCGATC AATTCTTCCT TCTTTTTCCT GTATAGCACT ACAGACTTCC      120

TCTGCACTAG AAGCCACTCG TGTCCCGATG CGTACGTCAC GGATGCAAAG CCCCAGGTCT      180

TTTACGCTGC CGGGTGTGTC TATATCTTCC ACAACATAAT CAACGCAAGC GTGAATATGG      240

ATACCAGAAA CAGAGGTAAC CCTGTATACT AAATGCTCTT CCAAAACATG TTGATTAACA      300

GGTAAGCGCC TAGCACTATC ACCATTATCA GCAACAACGC CTTCATGCGC AACGTAATGA      360

GCAGCGAGCT CAACTGGCAG AGATGACCCA CTACTGTTAC TCAAGATACT AGATAAGAGT      420

ACCCGGAGAT TTTCTGTGTT TACACCAGTT TTCTCCACAA TATTTGCAGC ATGCTTCGGC      480

TGTGACCTTA AGATTTCACG TATTTCATCG GAGTGTTGTA TGAAAAT                   527

(2) INFORMATION FOR SEQ ID NO: 22:

(i) SEQUENCE CHARACTERISTICS:
```

(A) LENGTH: 464 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 22:

| | | | | | |
|---|---|---|---|---|---|
| TTCACCTGGC | CAAATCTTAT | TGGATCTTCA | GGACAAAGAC | CAAGAATCTG | CTTCTCCAAG     60 |
| AAGCATTCTC | TGACCCCCAC | CTACCTATCT | GACTCTTAGC | TTAGATTCCT | AATGGTGTGA    120 |
| GTGTGTCAGA | GCCTTTACTT | AGTCTAAGCG | TAACTGTAAA | ACATCTTTT  | CAAAAGTCTC    180 |
| TGCATGACTG | TCTAGGTCTC | ACCTATCACA | CTGTAAGCAT | CTGGAAAACA | AAGCCACTGA    240 |
| GTCTTCCTTT | TACCAAAAAG | GCCTAGCCTT | GTTTTTGACA | AATGGCAAGA | ACACATTAGA    300 |
| TGTTTGTTGA | GAGAACAAAA | GGAGAGAACT | CATTATGAAA | CTCTGGACAA | CATTTATATA    360 |
| CCTCTCTACA | TTTTTTGTGT | TGGAGGTTAG | TTTTCTTTTC | TAATAATTTG | ATTTCTTTGG    420 |
| ATACATCGAG | GCAATACACT | TAAGAAGCAA | GAAGATTGGG | GGCC       |               464 |

(2) INFORMATION FOR SEQ ID NO: 23:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 23:

Tyr Gly Glu Arg Gly Asp Arg Ala Asn Trp Phe Tyr Met Leu Val Met
1               5                  10                  15

Ser Met Trp His Val Glu Met Leu Leu Arg Val Cys Ile Met Val Ile
            20                  25                  30

Cys Gln Gly Lys Val Tyr Phe Ile Glu Ala Glu Ala Gly Arg Ala Ala
        35                  40                  45

Thr Ala Glu Gly Gly Val Tyr Thr Thr Val Val Glu Ala Leu Ser Leu
    50                  55                  60

Val Gln Glu Glu Glu Gly Thr Gly Met Tyr Leu Ile Asn Ala Pro Glu
65                  70                  75                  80

Lys Ala Val Val Arg Phe Phe Lys Ile Glu Lys Ser Ala Ala Glu Glu
                85                  90                  95

Pro Gln Thr Val Asp Pro Ser Val Val Glu Ser Ala Thr Gly Ser Gly
            100                 105                 110

Val Asp Thr Gln Glu Glu Gln Glu Ile Asp Gln Glu Ala Pro Ala Ile
        115                 120                 125

Glu Glu Val Glu Thr Glu Gly Gln Glu Val Ile Leu Glu Glu Gly Thr
    130                 135                 140

Leu Ile Asp Leu Glu Gln Pro Val Ala Gln Val Pro Val Val Ala Glu
145                 150                 155                 160

Ala Glu Leu Pro Gly Val Glu Ala Ala Glu Ala Ile Val Pro Ser Leu
                165                 170                 175

Glu Glu Asn Lys Leu Gln Glu Val Val Val Ala Pro Glu Ala Gln Gln
            180                 185                 190

```
Leu Glu Ser Ala Pro Glu Val Ser Ala Pro Ala Gln Pro Glu Ser Thr
            195                 200                 205

Val Leu Gly Val Ala Glu Gly Asp Leu Lys Ser Glu Val Ser Val Glu
            210                 215                 220

Ala Asn Ala Asp Val Arg Lys Lys Lys
225                 230

(2) INFORMATION FOR SEQ ID NO: 24:

(i) SEQUENCE CHARACTERISTICS:
         (A) LENGTH: 376 amino acids
         (B) TYPE: amino acid
         (C) STRANDEDNESS: single
         (D) TOPOLOGY: linear (ii) MOLECULE TYPE: protein (vi) ORIGINAL SOURCE:
         (A) ORGANISM: Ehrlichia (xi) SEQUENCE DESCRIPTION: SEQ ID NO: 24:

Lys Gly Ala Pro Ala Thr Gln Arg Asp Ala Tyr Gly Lys Thr Ala Leu
1               5                   10                  15

His Ile Ala Ala Ala Asn Gly Asp Gly Lys Leu Tyr Lys Leu Ile Ala
            20                  25                  30

Lys Lys Cys Pro Asp Ser Cys Gln Ala Leu Leu Ser His Met Gly Asp
            35                  40                  45

Thr Ala Leu His Glu Ala Leu Tyr Ser Asp Lys Val Thr Glu Lys Cys
        50                  55                  60

Phe Leu Lys Met Leu Lys Glu Ser Arg Lys His Leu Ser Asn Ser Ser
65                  70                  75                  80

Phe Gly Asp Leu Leu Asn Thr Pro Gln Glu Ala Asn Gly Asp Thr Leu
                85                  90                  95

Leu His Leu Ala Ala Ser Arg Gly Phe Gly Lys Ala Cys Lys Ile Leu
            100                 105                 110

Leu Lys Ser Gly Ala Ser Val Ser Val Val Asn Val Glu Gly Lys Thr
            115                 120                 125

Pro Val Asp Val Ala Asp Pro Ser Leu Lys Thr Arg Pro Trp Phe Phe
            130                 135                 140

Gly Lys Ser Val Val Thr Met Met Ala Glu Arg Val Gln Val Pro Glu
145                 150                 155                 160

Gly Gly Phe Pro Pro Tyr Leu Pro Pro Glu Ser Pro Thr Pro Ser Leu
                165                 170                 175

Gly Ser Ile Ser Ser Phe Glu Ser Val Ser Ala Leu Ser Ser Leu Gly
            180                 185                 190

Ser Gly Leu Asp Thr Ala Gly Ala Glu Glu Ser Ile Tyr Glu Glu Ile
            195                 200                 205

Lys Asp Thr Ala Lys Gly Thr Thr Glu Val Glu Ser Thr Tyr Thr Thr
            210                 215                 220

Val Gly Ala Glu Glu Ser Ile Tyr Glu Glu Ile Lys Asp Thr Ala Lys
225                 230                 235                 240

Gly Thr Thr Glu Val Glu Ser Thr Tyr Thr Thr Val Gly Ala Glu Gly
                245                 250                 255

Pro Arg Thr Pro Glu Gly Glu Asp Leu Tyr Ala Thr Val Gly Ala Ala
                260                 265                 270

Ile Thr Ser Glu Ala Gln Ala Ser Asp Ala Ala Ser Ser Lys Gly Glu
            275                 280                 285
```

```
Arg Pro Glu Ser Ile Tyr Ala Asp Pro Phe Asp Ile Val Lys Pro Arg
    290                 295                 300
Gln Glu Arg Pro Glu Ser Ile Tyr Ala Asp Pro Phe Ala Ala Glu Arg
305                 310                 315                 320
Thr Ser Ser Gly Val Thr Thr Phe Gly Pro Lys Glu Glu Pro Ile Tyr
                325                 330                 335
Ala Thr Val Lys Lys Gly Pro Lys Lys Ser Asp Thr Ser Gln Lys Glu
            340                 345                 350
Gly Thr Ala Ser Glu Lys Val Gly Ser Thr Ile Thr Val Ile Lys Lys
        355                 360                 365
Lys Val Lys Pro Gln Val Pro Ala
    370                 375
```

(2) INFORMATION FOR SEQ ID NO: 25:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 25:

```
Tyr Glu Gly Gly Gly Glu Arg Val Glu Leu Pro Val Arg Gln Tyr Leu
1               5                   10                  15
Pro Ile Leu Met Leu Arg Val Asp Pro Met Met Leu Arg Val Asp Pro
            20                  25                  30
Thr Met Leu Lys Val Val His Thr Asn Arg Ala Ser Ser Leu Asp His
        35                  40                  45
Val Val Glu Tyr Ala Lys Leu Val Asp Phe Pro Phe Gln Arg His Phe
    50                  55                  60
Leu Thr Leu Met Leu Arg Val Asp Pro Thr Met Leu Lys Val Val His
65                  70                  75                  80
Thr Asn Arg Ala Ser Ser Leu Asp His Val Val Glu Tyr Ala Lys Leu
                85                  90                  95
Val Asp Phe Pro Phe Gln Arg His Phe Leu Thr Leu Met Leu Arg Val
            100                 105                 110
Asp Pro Thr Met Leu Lys Val Val His Thr Asn Arg Ala Ser Ser Leu
        115                 120                 125
Asp His Val Val Glu Tyr Ala Lys Leu Val Asp Phe Pro Phe Gln Arg
    130                 135                 140
His Phe Leu Thr
145
```

(2) INFORMATION FOR SEQ ID NO: 26:

(i) SEQUENCE CHARACTERISTICS:
        (A) LENGTH: 89 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 26:

```
Tyr Gly Ser Ser Lys Leu Gly Thr Thr Gly Phe Tyr Lys Arg Leu Val
1               5                   10                  15

Asp Ile Lys Pro Cys Glu Ile Ile Ala Ile Asn Ser Ser Phe Phe
            20                  25                  30

Leu Tyr Ser Thr Thr Asp Phe Leu Cys Thr Arg Ser His Ser Cys Pro
        35                  40                  45

Asp Ala Tyr Val Thr Asp Ala Lys Pro Gln Val Phe Tyr Ala Ala Gly
    50                  55                  60

Cys Val Tyr Ile Phe His Asn Ile Ile Asn Ala Ser Val Asn Met Asp
65              70                  75                  80

Thr Arg Asn Arg Gly Asn Pro Val Tyr
                85
```

(2) INFORMATION FOR SEQ ID NO: 27:

(i) SEQUENCE CHARACTERISTICS:
        (A) LENGTH: 238 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 27:

```
Leu Gly Ser Ala Ala Gly Thr Gly Ser Gln Gln Ala Ser His Ile Pro
1               5                   10                  15

Pro His Asp Pro Gly Met Met Pro Tyr Ser Tyr Ala Gln Pro Ser Thr
            20                  25                  30

Ser Trp Asp Gln Pro Ser Thr Ser Gly Leu Gly Ser Ala Ala Gly Met
        35                  40                  45

Gly Ser Gln Gln Ala Ser His Ile Pro Pro His Asp Pro Gly Met Met
    50                  55                  60

Pro Tyr Ser Tyr Ala Gln Pro Ser Thr Ser Trp Asp Gln Pro Ser Thr
65              70                  75                  80

Ser Gly Leu Gly Ser Ala Ala Gly Met Gly Ser Gln Gln Ala Ser His
            85                  90                  95

Ile Pro Pro His Asp Pro Gly Met Met Pro Tyr Ser Tyr Ala Gln Pro
            100                 105                 110

Ser Thr Ser Trp Asp Gln Pro Ser Thr Ser Trp Asp Gln Pro Ser Thr
        115                 120                 125

Ser Gly Leu Gly Gly Thr Ala Gly Gln Gly Ala Gln Leu Val Pro Pro
    130                 135                 140

Pro Pro His Ile Ile Leu Arg Val Leu Glu Asn Val Pro Tyr Pro Ser
145             150                 155                 160

Ser Gln Phe Ser Thr Ser Gly Leu Gly Gly Thr Ser Thr Gly Met Gly
            165                 170                 175

Arg Ser Gln Ala Pro Tyr Val Pro Pro Gln Asp Gln Gly Ile Met Pro
            180                 185                 190

Tyr Ser Trp Asp Gln Pro Ser Ala Ser Gly Leu Gly Gly Ala Ser Tyr
        195                 200                 205

Thr Leu Glu Glu Ala Gln Val Ser Ser His Arg Pro Arg Thr Pro Ser
    210                 215                 220

Asp Asp Asp Ser Glu Pro Pro Ser Lys Gln Ala Arg Arg Ala
```

```
225             230             235
```

(2) INFORMATION FOR SEQ ID NO: 28:

(i) SEQUENCE CHARACTERISTICS:
        (A) LENGTH: 334 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 28:

```
Ser Trp Gln Lys Thr Thr Cys Leu Leu Met Ser Leu Phe Arg Ile Lys
1               5                   10                  15

Lys Val Asp Val Glu Ile Lys Asn Ser Glu Leu His Asp Gln Arg Asp
            20                  25                  30

Val Leu Asn Leu Val Phe Thr Asp Lys Asn Glu Ala Glu Leu Ala Tyr
        35                  40                  45

Lys Ala Tyr Gln Glu Gly Lys Ser Phe Glu Glu Leu Val Ser Asp Ala
    50                  55                  60

Gly Tyr Thr Ile Glu Asp Ile Ala Leu Asn Asn Ile Ser Lys Asp Val
65                  70                  75                  80

Leu Pro Val Gly Val Arg Asn Val Val Phe Ala Leu Asn Glu Gly Glu
                85                  90                  95

Val Ser Glu Met Phe Arg Ser Val Val Gly Trp His Ile Met Lys Val
            100                 105                 110

Ile Arg Lys His Glu Ile Thr Lys Glu Asp Leu Glu Lys Leu Lys Glu
        115                 120                 125

Lys Ile Ser Ser Asn Ile Arg Arg Gln Lys Ala Gly Glu Leu Leu Val
    130                 135                 140

Ser Asn Val Lys Lys Ala Asn Asp Met Ile Ser Arg Gly Ala Leu Leu
145                 150                 155                 160

Asn Glu Leu Lys Asp Met Phe Gly Ala Arg Ile Ser Gly Val Leu Thr
                165                 170                 175

Asn Phe Asp Met His Gly Leu Asp Lys Ser Gly Asn Leu Val Lys Asp
            180                 185                 190

Phe Pro Leu Gln Leu Gly Ile Asn Ala Phe Thr Thr Leu Ala Phe Ser
        195                 200                 205

Ser Ala Val Gly Lys Pro Ser His Leu Val Ser Asn Gly Asp Ala Tyr
    210                 215                 220

Phe Gly Val Leu Val Thr Glu Val Val Pro Arg Pro Arg Thr Leu
225                 230                 235                 240

Glu Glu Ser Arg Ser Ile Leu Thr Glu Glu Trp Lys Ser Ala Leu Arg
                245                 250                 255

Met Lys Lys Ile Arg Glu Phe Ala Val Glu Leu Arg Ser Lys Leu Gln
            260                 265                 270

Asn Gly Thr Glu Leu Ser Val Val Asn Gly Val Ser Phe Lys Lys Asn
        275                 280                 285

Val Thr Val Lys Lys Ser Asp Gly Ser Thr Asp Asn Asp Ser Lys Tyr
    290                 295                 300

Pro Glu Arg Leu Val Asp Glu Ile Phe Ala Ile Asn Ile Gly Gly Val
305                 310                 315                 320

Thr Lys Glu Val Ile Asp Ser Glu Ser Glu Thr Val Tyr Ile
```

(2) INFORMATION FOR SEQ ID NO: 29:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 29:

```
Ile Phe Ile Gln His Ser Asp Glu Ile Arg Glu Ile Leu Arg Ser Gln
1               5                   10                  15
Pro Lys His Ala Ala Asn Ile Val Glu Lys Thr Gly Val Asn Thr Glu
            20                  25                  30
Asn Leu Arg Val Leu Leu Ser Ser Ile Leu Ser Asn Ser Ser Gly Ser
        35                  40                  45
Ser Leu Pro Val Glu Leu Ala Ala His Tyr Val Ala His Glu Gly Val
    50                  55                  60
Val Ala Asp Asn Gly Asp Ser Ala Arg Arg Leu Pro Val Asn Gln His
65                  70                  75                  80
Val Leu Glu Glu His Leu Val Tyr Arg Val Thr Ser Val Ser Gly Ile
                85                  90                  95
His Ile His Ala Cys Val Asp Tyr Val Val Glu Asp Ile Asp Thr Pro
            100                 105                 110
Gly Ser Val Lys Asp Leu Gly Leu Cys Ile Arg Asp Val Arg Ile Gly
        115                 120                 125
Thr Arg Val Ala Ser Ser Ala Glu Glu Val Cys Ser Ala Ile Gln Glu
    130                 135                 140
Lys Glu Gly Arg Ile Asp Arg Asn Asp Phe Ala Trp Phe Asn Val Asp
145                 150                 155                 160
Gln Ser Leu Val Glu Thr Ser Arg Ala Glu Phe Arg Ala Ala Ile
                165                 170                 175
```

(2) INFORMATION FOR SEQ ID NO: 30:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Ehrlichia (ix) FEATURE:
        (A) NAME/KEY: Modified-site
        (B) LOCATION: 7
        (D) OTHER INFORMATION: /note= "Where Xaa is either a Met
           or Thr"

(xi) SEQUENCE DESCRIPTION: SEQ ID NO: 30:

```
Leu Gly Ser Ala Ala Gly Xaa Gly Ser Gln Gln Ala Ser His Ile Pro
1               5                   10                  15
Pro His Asp Pro Gly Met Met Pro Tyr Ser Tyr Ala Gln Pro Ser Thr
            20                  25                  30
```

Ser Trp Asp Gln Pro Ser Thr Ser Gly
         35                  40

(2) INFORMATION FOR SEQ ID NO: 31:

(i) SEQUENCE CHARACTERISTICS:
        (A) LENGTH: 860 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 31:

```
AAAAGCTTAA GGAAGATGTG GCTTCTATGT CGGATGAGGC TTTGCTGAAG TTTGCCAATA      60

GGCTCAGAAG AGGTGTTCCT ATGGCTGCTC CGGTGTTTGA GGGTCCGAAG GATGCGCAGA     120

TTTCCCGGCT TTTGGAATTA GCGGATGTTG ATCCGTCTGG GCAGGTGGAT CTTTATGATG     180

GGCGTTCAGG GCAGAAGTTT GATCGCAAGG TAACTGTTGG ATACATTTAC ATGTTGAAGC     240

TCCATCACTT GGTGGATGAC AAGATACATG CTAGGTCTGT TGGTCCGTAT GGTCTGGTTA     300

CTCAGCAACC TCTTGGAGGA AAGTCGCACT TTGGTGGGCA GAGATTTGGG GAAATGGAAT     360

GCTGGGCATT GCAGGCCTAT GGTGCTGCTT ATACTTTGCA GGAAATGCTA ACTGTCAAAT     420

CTGACGATAT CGTAGGTAGG GTAACAATCT ATGAATCCAT AATTAAGGGG GATAGCAACT     480

TCGAGTGTGG TATTCCTGAG TCGTTTAATG TCATGGTCAA GGAGTTACGC TCGCTGTGCC     540

TTGATGTTGT TCTAAAGCAG GATAAAGAGT TTACTAGTAG CAAGGTGGAG TAGGGATTTA     600

CAATTATGAA GACGTTGGAT TTGTATGGCT ATACCAGTAT AGCACAGTCG TTCGATAACA     660

TTTGCATATC CATATCTAGT CCACAAAGTA TAAGGGCTAT GTCCTATGGA GAAATCAAGG     720

ATATCTCTAC TACTATCTAT CGTACCTTTA AGGTGGAGAA GGGGGGGCTA TTCTGTCCTA     780

AGATCTTTGG TCCGGTTAAT GATGACGAGT GTCTTTGTGG TAAGTATAGG AAAAAGCGCT     840

ACAGGGGCAT TGTCTGTGAA                                                 860
```

(2) INFORMATION FOR SEQ ID NO: 32:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 32:

Lys Leu Lys Glu Asp Val Ala Ser Met Ser Asp Glu Ala Leu Leu Lys
 1               5                  10                  15

Phe Ala Asn Arg Leu Arg Arg Gly Val Pro Met Ala Ala Pro Val Phe
                20                  25                  30

Glu Gly Pro Lys Asp Ala Gln Ile Ser Arg Leu Leu Glu Leu Ala Asp
             35                  40                  45

Val Asp Pro Ser Gly Gln Val Asp Leu Tyr Asp Gly Arg Ser Gly Gln
         50                  55                  60

Lys Phe Asp Arg Lys Val Thr Val Gly Tyr Ile Tyr Met Leu Lys Leu
65                  70                  75                  80

```
His His Leu Val Asp Asp Lys Ile His Ala Arg Ser Val Gly Pro Tyr
            85                  90                  95

Gly Leu Val Thr Gln Gln Pro Leu Gly Gly Lys Ser His Phe Gly Gly
            100                 105                 110

Gln Arg Phe Gly Glu Met Glu Cys Trp Ala Leu Gln Ala Tyr Gly Ala
            115                 120                 125

Ala Tyr Thr Leu Gln Glu Met Leu Thr Val Lys Ser Asp Asp Ile Val
            130                 135             140

Gly Arg Val Thr Ile Tyr Glu Ser Ile Ile Lys Gly Asp Ser Asn Phe
145                 150                 155                 160

Glu Cys Gly Ile Pro Glu Ser Phe Asn Val Met Val Lys Glu Leu Arg
                165                 170                 175

Ser Leu Cys Leu Asp Val Val Leu Lys Gln Asp Lys Glu Phe Thr Ser
            180                 185                 190

Ser Lys Val Glu
        195

(2) INFORMATION FOR SEQ ID NO: 33:

(i) SEQUENCE CHARACTERISTICS:
        (A) LENGTH: 89 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 33:

Gly Phe Thr Ile Met Lys Thr Leu Asp Leu Tyr Gly Tyr Thr Ser Ile
1               5                   10                  15

Ala Gln Ser Phe Asp Asn Ile Cys Ile Ser Ile Ser Ser Pro Gln Ser
            20                  25                  30

Ile Arg Ala Met Ser Tyr Gly Glu Ile Lys Asp Ile Ser Thr Thr Ile
            35                  40                  45

Tyr Arg Thr Phe Lys Val Glu Lys Gly Gly Leu Phe Cys Pro Lys Ile
    50                  55                  60

Phe Gly Pro Val Asn Asp Asp Glu Cys Leu Cys Gly Lys Tyr Arg Lys
65                  70                  75                  80

Lys Arg Tyr Arg Gly Ile Val Cys Glu
                85

(2) INFORMATION FOR SEQ ID NO: 34:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 34:

ATCATAAGCT TTACATGTCC TATCCAGGCG ATTATCCCTA TCCATAGCAT AGTAACGCCC      60

TGCAACAGTA GCAATTTCGG CATTTAAGTG CTCAATTTTA GCGTTCAGCA TACCGATATA    120
```

```
CTTCTCAGCA GAACGCGGTG GAACATCCCT ACCATCTAGA ATTACATGTA TAAAAACCTT      180

GATGCCAAAT CCGGTGATAA CCTCAATAAT GGTTTCCATG TGCGCCTGAA GAGAATGCAC      240

TCCACCATCA GAAAGCAGAC CAATCATGTG GCATACCCCA CCCTTCGCCT GTATATCGCG      300

CACAAAGTCC AACAATTTAG GATTCTTGTG AACCTCATTA ATCTCAAGAT TAATTCTCAA      360

CAGATCCTGA AGCACTATCC TGCCGCATCC TATACTTATG TGCCCTACTT CTGAATTCCC      420

GAACTGACCT GAAGGCAATC CGACATCCGT TCCACTAGCA GACAAACTAC TCATAGGACA      480

GCAT                                                                  484

(2) INFORMATION FOR SEQ ID NO: 35:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 35:

Cys Cys Pro Met Ser Ser Leu Ser Ala Ser Gly Thr Asp Val Gly Leu
1               5                   10                  15

Pro Ser Gly Gln Phe Gly Asn Ser Glu Val Gly His Ile Ser Ile Gly
            20                  25                  30

Cys Gly Arg Ile Val Leu Gln Asp Leu Leu Arg Ile Asn Leu Glu Ile
        35                  40                  45

Asn Glu Val His Lys Asn Pro Lys Leu Leu Asp Phe Val Arg Asp Ile
50                  55                  60

Gln Ala Lys Gly Gly Val Cys His Met Ile Gly Leu Leu Ser Asp Gly
65                  70                  75                  80

Gly Val His Ser Leu Gln Ala His Met Glu Thr Ile Ile Glu Val Ile
                85                  90                  95

Thr Gly Phe Gly Ile Lys Val Phe Ile His Val Ile Leu Asp Gly Arg
            100                 105                 110

Asp Val Pro Pro Arg Ser Ala Glu Lys Tyr Ile Gly Met Leu Asn Ala
        115                 120                 125

Lys Ile Glu His Leu Asn Ala Glu Ile Ala Thr Val Ala Gly Arg Tyr
    130                 135                 140

Tyr Ala Met Asp Arg Asp Asn Arg Leu Asp Arg Thr Cys Lys Ala Tyr
145                 150                 155                 160

Asp (2) INFORMATION FOR SEQ ID NO: 36:

(i) SEQUENCE CHARACTERISTICS:
        (A) LENGTH: 1039 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Ehrlichia (xi) SEQUENCE DESCRIPTION: SEQ ID NO: 36:

TTAATCAGAG CGGTTGTGCT AGTCCTTTCC GAAATTCCTG TGCTGAATGC GGAGATTTCA       60
```

```
GGCGATGATA TAGTCTACAG GGACTATTGT AACATTGGAG TCGCGGTAGG TACCGATAAG      120

GGGTTAGTGG TGCCTGTTAT CAGAAGAGCG GAAACTATGT CACTTGCTGA AATGGAGCAA      180

GCACTTGTTG ACTTAAGTAC AAAAGCAAGA AGTGGCAAGC TCTCTGTTTC TGATATGTCT      240

GGTGCAACCT TTACTATTAC CAATGGTGGT GTGTATGGGT CGCTATTGTC TACCCCTATA      300

ATCAACCCTC CTCAATCTGG AATCTTGGGT ATGCATGCTA TACAGCAGCG TCCTGTGGCA      360

GTAGATGGTA AGGTAGAGAT AAGGCCTATG ATGTATTTGG CGCTATCATA TGATCATAGA      420

ATAGTTGACG GGCAAGGTGC TGTGACGTTT TTGGTAAGAG TGAAGCAGTA CATAGAAGAT      480

CCTAACAGAT TGGCTCTAGG AATTTAGGGG GTTTTTATGG GGCGGGGTAC AATAACCATC      540

CACTCCAAAG AGGATTTTGC CTGTATGAGA AGGGCTGGGA TGCTTGCAGC TAAGGTGCTT      600

GATTTTATAA CGCCGCATGT TGTTCCTGGT GTGACTACTA ATGCTCTGAA TGATCTATGT      660

CACGATTTCA TCATTTCTGC CGGGGCTATT CCAGCGCCTT TGGGCTATAG AGGGTATCCT      720

AAGTCTATTT GTACTTCGAA GAATTTTGTG GTTTGCCATG GCATTCCAGA TGATATTGCA      780

TTAAAAAACG GCGATATAGT TAACATAGAC GTTACTGTGA TCCTCGATGG TTGGCACGGG      840

GATACTAATA GGATGTATTG GGTTGGTGAT AACGTCTCTA TTAAGGCTAA GCGCATTTGT      900

GAGGCAAGTT ATAAGGCATT GATGGCGGCG ATTGGTGTAA TACAGCCAGG TAAGAAGCTC      960

AATAGCATAG GGTTAGCTAT AGAGGAAGAA ATCAGAGGTT ATGGATACTC CATTGTTAGA     1020

GATTACTGCG GACATGGGA                                                  1039

(2) INFORMATION FOR SEQ ID NO: 37:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 37:

Leu Ile Arg Ala Val Val Leu Val Leu Ser Glu Ile Pro Val Leu Asn
1               5                   10                  15

Ala Glu Ile Ser Gly Asp Asp Ile Val Tyr Arg Asp Tyr Cys Asn Ile
            20                  25                  30

Gly Val Ala Val Gly Thr Asp Lys Gly Leu Val Val Pro Val Ile Arg
        35                  40                  45

Arg Ala Glu Thr Met Ser Leu Ala Glu Met Glu Gln Ala Leu Val Asp
    50                  55                  60

Leu Ser Thr Lys Ala Arg Ser Gly Lys Leu Ser Val Ser Asp Met Ser
65                  70                  75                  80

Gly Ala Thr Phe Thr Ile Thr Asn Gly Val Tyr Gly Ser Leu Leu
                85                  90                  95

Ser Thr Pro Ile Ile Asn Pro Pro Gln Ser Gly Ile Leu Gly Met His
            100                 105                 110

Ala Ile Gln Gln Arg Pro Val Ala Val Asp Gly Lys Val Glu Ile Arg
        115                 120                 125

Pro Met Met Tyr Leu Ala Leu Ser Tyr Asp His Arg Ile Val Asp Gly
    130                 135                 140

Gln Gly Ala Val Thr Phe Leu Val Arg Val Lys Gln Tyr Ile Glu Asp
```

-continued

```
145                 150                 155                 160
Pro Asn Arg Leu Ala Leu Gly Ile
                165

(2) INFORMATION FOR SEQ ID NO: 38:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ehrlichia (xi) SEQUENCE DESCRIPTION: SEQ ID NO: 38:

Gly Val Phe Met Gly Arg Gly Thr Ile Thr Ile His Ser Lys Glu Asp
1               5                   10                  15

Phe Ala Cys Met Arg Arg Ala Gly Met Leu Ala Ala Lys Val Leu Asp
                20                  25                  30

Phe Ile Thr Pro His Val Val Pro Gly Val Thr Thr Asn Ala Leu Asn
            35                  40                  45

Asp Leu Cys His Asp Phe Ile Ile Ser Ala Gly Ala Ile Pro Ala Pro
    50                  55                  60

Leu Gly Tyr Arg Gly Tyr Pro Lys Ser Ile Cys Thr Ser Lys Asn Phe
65                  70                  75                  80

Val Val Cys His Gly Ile Pro Asp Asp Ile Ala Leu Lys Asn Gly Asp
                85                  90                  95

Ile Val Asn Ile Asp Val Thr Val Ile Leu Asp Gly Trp His Gly Asp
                100                 105                 110

Thr Asn Arg Met Tyr Trp Val Gly Asp Asn Val Ser Ile Lys Ala Lys
            115                 120                 125

Arg Ile Cys Glu Ala Ser Tyr Lys Ala Leu Met Ala Ala Ile Gly Val
    130                 135                 140

Ile Gln Pro Gly Lys Lys Leu Asn Ser Ile Gly Leu Ala Ile Glu Glu
145                 150                 155                 160

Glu Ile Arg Gly Tyr Gly Tyr Ser Ile Val Arg Asp Tyr Cys Gly His
                165                 170                 175

Gly
```